United States Patent [19]

Clemens et al.

[11] 4,054,660

[45] Oct. 18, 1977

[54] METHOD OF INHIBITING PROLACTIN

[75] Inventors: James A. Clemens; Edmund C. Kornfeld; Nicholas J. Bach, all of Indianapolis, Ind.

[73] Assignee: Eli Lilly and Company, Indianapolis, Ind.

[21] Appl. No.: 715,774

[22] Filed: Aug. 19, 1976

Related U.S. Application Data

[60] Continuation-in-part of Ser. No. 568,072, April 14, 1975, abandoned, which is a division of Ser. No. 419,566, Nov. 28, 1973, Pat. No. 3,920,664, which is a continuation-in-part of Ser. No. 273,902, July 21, 1972, abandoned.

[51] Int. Cl.² .................................................. A61K 31/48
[52] U.S. Cl. .................................................. 424/261
[58] Field of Search ........................................ 424/261

[56] References Cited

U.S. PATENT DOCUMENTS

| 2,516,002 | 7/1950 | Hofmann et al. | 260/285.5 |
| 3,732,231 | 5/1973 | Smonsky et al. | 260/285.5 |
| 3,752,814 | 8/1973 | Fluckiger et al. | 260/285.5 |

OTHER PUBLICATIONS

Chemical Abstracts 70:219(r) (1969).

*Primary Examiner*—Jerome D. Goldberg
*Attorney, Agent, or Firm*—James L. Rowe; Everet F. Smith

[57] ABSTRACT

D-2-halo-6-alkyl-8-substituted ergolines and related compounds are inhibitors of prolactin in mammals.

2 Claims, No Drawings

METHOD OF INHIBITING PROLACTIN

CROSS-REFERENCE

This application is a continuation-in-part of our copending application, Ser. No. 568,072, filed Apr. 14, 1975 now abandoned, which was in turn a division of our then copending application, Ser. No. 419,566 filed Nov. 28, 1973, now U.S. Pat. No. 3,920,664, issued Nov. 18, 1975, which was in turn a continuation-in-part of our application Ser. No. 273,902, filed July 21, 1972, now abandoned.

BACKGROUND OF THE INVENTION

Compounds based on the ergoline ring system (I):

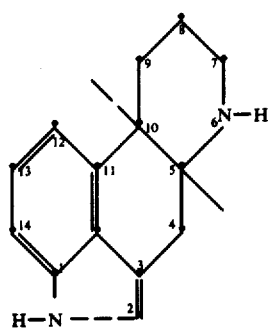

have a surprising variety of pharmaceutical activities. For example, lysergic and isolysergic acid are 8-carboxy-6-methyl-$\Delta^9$-ergolines. The amides of lysergic acid, many of which have valuable and unique pharmacologic properties, include the naturally occurring oxytocic alkaloids — ergocornine, ergokryptine, ergonovine, ergocristine, ergosine, ergotamine etc. — and synthetic oxytocics such as methergine as well as the synthetic hallucinogen — lysergic acid diethylamide or LSD. The amides of 6-methyl-8-carboxyergoline, known generically as dihydroergot alkaloids, are oxytocic agents of lower potency and also lower toxicity than the ergot alkaloids themselves. Ergotamine, a $\Delta^9$-ergoline, has been used in the treatment of migraine and recently, both ergocornine and 2-bromo-α-ergokryptine have been shown to be inhibitors of prolactin and of dimethylbenzanthracene (DMBA)-induced tumors in rats, according to Nagasawa and Meites, *Proc. Soc. Exp'tl. Biol. Med.* 135, 469 (1970) and to Heuson et al., *Europ. J. Cancer*, 353, (1970). (See also U.S. Pat. Nos. 3,752,888 and 3,752,814).

D-6-methyl-8-cyanomethylergoline was first prepared by Semonsky and co-workers, *Coll. Czech. Chem. Commun.*, 33, 577 (1968), and its use in preventing pregnancy in rats was published by the same group in *Nature*, 221, 666 (1969). (See also U.S. Pat. No. 3,732,231). The compound was thought to interfere with the secretion of hypophysial leuteotropic hormone and the hypophysial gonadotropins. It was also suggested that the compound inhibited the secretion of prolactin. [See Seda et al., *Reprod. Fert.*, 24, 263 (1971) and Mantle and Finn, id. 441)]. Semonsky and co-workers, *Coll. Czech. Chem. Comm.*, 36, 220 (1971), described the preparation of D-6-methyl-8-ergolinylacetamide, a compound which is stated to have anti-fertility and anti-lactating effects on rats. The effect of these compounds in neoplastic disease is unknown.

Ergolines having a group other than methyl in the 6-position have been prepared by Fehr et al., *Helv. Chim. Acta,* 53, 2197 (1971) and Nakaharo et al., *Chem. Pharm. Bull.,* 19, 2337 (1971).

SUMMARY OF THE INVENTION

This invention provides a process for inhibiting the secretion of prolactin in mammals employing a D-6-alkyl 2,8-disubstituted ergolines represented by the following formula:

II

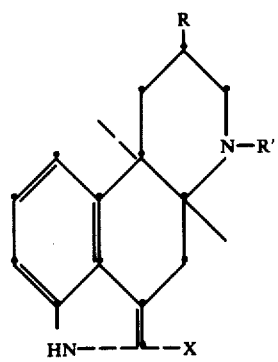

wherein X is Cl, Br or I; R is $CH_2$—CN or

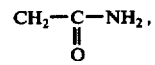

and R' is $C_1$–$C_3$ primary alkyl.

Also useful in the process of this invention are the non-toxic salts of the above ergoline bases formed with pharmaceutically-acceptable acids.

In the above formula, when R' is $C_1$–$C_3$ primary alkyl, it represents methyl, ethyl and n-propyl.

The prefix "D" in the naming of the compounds of the above structure indicates that the sterochemistry of the ergoline derivative is identical to that of D-lysergic acid—the naturally-occuring form.

Non-toxic salts of the ergolines represented by the above formula can be formed with both organic and inorganic pharmaceutically-acceptable acids. Such salts include sulfates, such as sulfate, pyrosulfate, and bisulfate; sulfites, such as sulfite and bisulfite; nitrate; phosphates, such as phosphate, monohydrogenphosphate, dihydrogenphosphate, metaphosphate and pyrophosphate; halides, such as chloride, bromide and iodide; $C_1$–$C_{10}$ aliphatic carboxylates, such as acetate, propionate, decanoate, caprylate, acrylate, formate, isobutyrate, caprate, heptanoate and propiolate; $C_1$–$C_{10}$ aliphatic dicarboxylates, such as oxalate, malonate, succinate, suberate, sebacate, fumarate, maleate, butyne-1,4-dioate and hexyne-1,6-dioate; benzoates, such as benzoate, chlorobenzoate, methylbenzoate, dinitrobenzoate, hydroxybenzoate and methoxybenzoate; phthalates, such as phthalate and terephthalate; arylsulfonates, such as toluenesulfonate, benzenesulfonate, naphthalenesulfonate, p-chlorobenzenesulfonate and xylenesulfonate; citrate; $C_2$–$C_5$ α-hydroxyalkanoates, such as lactate, β-hydroxybutyrate and glycollate; $C_4$–$C_6$ α-hydroxyalkanedioates, such as malate and tartrate; and $C_1$–$C_3$ alkylsulfonates, such as methanesulfonate and propanesulfonate.

Compounds according to the above formula in which X is a halogen and R' is methyl are prepared by the action of N-bromosuccinimide, N-chlorosuccinimide or other positive halogenating agent on D-6-methyl-8-cyanomethylergoline or D-6-methyl-8-carboxamidomethylergoline—prepared by the methods of Semonsky and co-workers (loc. cit.). Alternatively, compounds in which R is $CH_2$—CN and R' is methyl can be prepared by the reaction of a positive halogenating agent on a D-6-methyl-8-halomethylergoline followed by replacement of the halogen atom of the halomethyl group with a cyano group, using sodium cyanide or like reagent to effect the displacement. Conversion of the thus formed cyano group to an amide group can be carried out by procedures well known in the art. Similar halogenation of D-6-methyl-8-mesyloxymethyl (or 8-tosyloxymethyl)ergoline in the 2-position readily yields an intermediate which will react with sodium cyanide or other like inorganic cyanide in an inert solvent to yield compounds coming within the scope of the above formula.

Compounds in which R' is other than methyl are preferably prepared by reacting with cyanogen bromide, a compound in which X and R are defined as above and R' is methyl. A suitable inert solvent such as methylene dichloride is customarily used. The product of this reaction is a 6-cyano derivative in which the groups at 8 and 2 remain unchanged. Reduction or hydrolysis of the 6-cyano derivative produces the secondary amine compound (III)

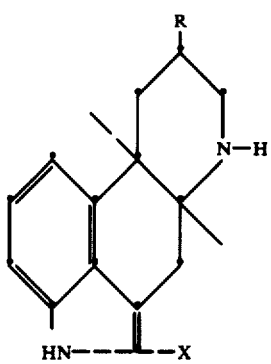

III in which X and R are defined as hereinabove. Alkylation of this secondary amine by an alkyl halide (R'—Hal wherein Hal is preferably chloro, bromo or iodo) in a suitable inert solvent produces a compound of formula II above. The above procedure is useful not only in preparing the hitherto unavailable 6-alkyl ergolines wherein the alkyl group is other than methyl but is also useful in the case where the alkyl group (R') is methyl in preparing radioactive-labeled ergoline derivatives of formula II above in which the radioactive tag is a $C^{14}$ atom located in the $C_6$ methyl group. Alternatively, the methyl group of a D-6-methyl-8-substituted ergoline can be replaced with a higher alkyl group by the above procedure to yield a D-6-alkyl-8-substituted ergoline, which latter compound can then be halogenated or otherwise substituted in the 2-position of the ergoline ring by the procedures set forth above for the 6-methyl ergolines to yield 6-alkyl compounds of Formula II above, in which R' is other than methyl.

The compounds useful in the novel processes of this invention can be prepared as follows.

EXAMPLE 1

Preparation of D-2-chloro-6-methyl-8-cyanomethylergoline

Four-hundred milligrams of N-chlorosuccinimide were dissolved in 30 ml. of dioxane and the solution added in dropwise fashion at a temperature of about 60° C. to a stirred suspension of 535 mg. of D-6-methyl-8-cyanomethylergoline dissolved in 25 ml. of dioxane. After the addition had been completed, the reaction mixture was heated under a nitrogen atmosphere in the range 60°–65° C. for a period of about 4.5 hours. The reaction mixture was then cooled and diluted with water. Solid sodium bicarbonate was added to the mixture which was then extracted with chloroform. The chloroform layer was separated and dried, and the chloroform removed by evaporation in vacuo. The resulting crude residue showed the presence of 2 spots in thin-layer chromatography. The residue was therefore dissolved in chloroform and chromatographed over florisil. Thin-layer chromatography carried out on each of the chloroform eluate fractions indicated that fractions 7–12 had the largest amounts of a new component, (not starting material). The fractions showing a relatively large amount of this new component by thin-layer chromatography were combined and the chloroform evaporated therefrom. The resulting residue, on recrystallization from ether, yielded 165 mg. of D-2-chloro-6-methyl-8-cyanomethylergoline melting at 270–3° C.

Analysis: Calc: C, 68.11; H, 6.05; H, 14.02; Cl, 11.83. Found: C, 67.82; H, 6.14; N, 13.81; C., 11.77.

Following the above procedure, D-6-methyl-8-cyanomethylergoline was brominated with N-bromosuccinimide to yield D-2-bromo-6-methyl-8-cyanomethylergoline melting at about 244–7° C. with decomposition after recrystallization from ethanol.

Analysis: Calc: C, 59.31; H, 5.27; N, 12.21; Br, 23.21. Found: C, 59.33; H, 5.37; N, 11.96; Br, 23.39.

Following the above procedure, D-6-methyl-8-cyanomethylergoline was reacted with N-iodosuccinimide to yield D-2-iodo-6-methyl-8-cyanomethylergoline melting at about 211°–213° C. with decomposition after recrystallization from ether.

Analysis: Calc: C, 52.19; H, 4.64; N, 10.74; I, 32.44. Found: C, 51.90; H, 4.51; N, 10.58; I, 32.17.

EXAMPLE 2

Preparation of D-2-bromo-6-methyl-8-carboxamidomethylergoline

A solution containing 240 mg. of D-6-methyl-8-carboxamidoergoline and 25 ml. of dioxane was prepared at a temperature in the range 65°–70° C. under a nitrogen atmosphere. A solution containing 180 mg. of N-bromosuccinimide in 20 ml. of dioxane was added in dropwise fashion. The resulting mixture was heated at the same temperature range with stirring for about one-half hour and was then poured over saturated aqueous tartaric acid. The resulting mixture was extracted with chloroform, and the chloroform layer discarded. The aqueous layer was filtered and then made basic with dilute ammonium hydroxide. D-2-bromo-6-methyl-8-carboxamidomethylergoline formed in the above reaction was insoluble in the aqueous alkaline solution and separated. The separation compound was dissolved in chloroform. The chloroform layer was separated and dried. Evaporation of the solvents in vacuo yielded D-2-bromo-6-methyl-8-carboxamidomethylergoline

EXAMPLE 3

Preparation of D-6-methyl-8-bromomethylergoline

A solution of 5.2 g. of triphenylphosphine dissolved in 100 ml. of acetonitrile was placed under a nitrogen atmosphere and stirring initiated. 1.0 ml. of bromine was added in dropwise fashion to the triphenyphosphine solution. After the addition had been completed slight warming yielded a clear, colorless solution indicating completion of the reaction. 505 mg. of D-6-methyl-8-hydroxymethylergoline was added all at once to the triphenylphosphoniumbromide solution. The reaction mixture was stirred for about 6.5 hours at room temperature protected by a calcium chloride drying tube. The solution was then poured into saturated aqueous sodium bicarbonate and the organic material extracted with chloroform. The chloroform layer was then contacted with saturated aqueous tartaric acid, thereby forming water-soluble tartrate salts of the ergoline bases present. The water layer was separated, the chloroform layer being discarded. The water layer was then made basic with solid sodium bicarbonate. The ergoline base, being insoluble in the aqueous alkaline solution, separated and was dissolved in chloroform. The chloroform layer was separated and dried. Evaporation of the chloroform in vacuo yielded a residue comprising D-6-methyl-8-bromomethylergoline formed in the above reaction.

Analysis: Calc: C, 60.20; H, 6.00; N, 8.78; Br, 25.03. Found: C, 60.11; H, 6.06; N, 8.59; Br, 25.35.

EXAMPLE 4

Preparation of D-6-methyl-8-cyanomethylergoline

A suspension of 10 g. of D-6-methyl-8-hydroxymethylergoline in 200 ml. of pyridine was prepared. To this suspension was added slowly a solution containing 6.0 ml. of methanesulfonyl chloride and 200 ml. of pyridine. The resulting mixture was stirred at room temperature under a nitrogen atmosphere for about one-half hour and was then poured into 2.5 l. of saturated aqueous sodium bicarbonate. The alkaline aqueous layer was diluted to 6 liters with water and the diluted layer allowed to stand at room temperature. D-6-methyl-8-mesyloxymethylergoline formed in the above reaction crystallized. The solution was chilled to about 0° C. in order to cause more of the desired material to precipitate. The solution was then filtered and the filter cake recrystallized from ethanol. A further quantity of D-6-methyl-8-mesyloxymethylergoline was obtained by extracting the filtrate with ethyl acetate, separating the ethyl acetate layer and removing the ethyl acetate by evaporation in vacuo. Recrystallization of D-6-methyl-8-mesyloxymethylergoine prepared as above from ethanol yielded material melting at about 192-4° C. with decomposition.

Analysis: Calc: C, 61.05; H, 6.63; N, 8.38; S, 9.59. Found: C, 60.85; H, 6.46; N, 8.45; S, 9.30.

12.5 g. of D-6-methyl-8-mesyloxymethylergoline prepared as above was heated with 12 g. of sodium cyanide in the presence of 350 ml. of DMSO at 100°–105° C. under a nitrogen atmosphere for 45 minutes. The reaction mixture was poured into 2 l. of saturated aqueous sodium chloride and the resulting mixture filtered. The solid material thus obtained was slurried in warm water and refiltered to give about 8.4 g. of D-6-methyl-8-cyanomethylergoline.

EXAMPLE 5

Alternate preparation of D-2-bromo-6-methyl-8-cyanomethylergoline

A solution of 955 mg. of D-6-methyl-8-bromomethylergoline, prepared by the procedure of Example 3, in 50 ml of dioxane was heated to 60°–65° C. under a nitrogen atmosphere. A solution of 600 mg. of N-bromosuccinimide in 70 ml. of dioxane was added in dropwise fashion. The reaction mixture was heated at 60°–65° C. for an additional half hour after all the N-bromosuccinimide had been added. The reaction mixture was then cooled and aqueous tartaric acid added thus forming water-soluble tartrate salts of the ergoline bases present. The resulting mixture was extracted with chloroform, and the chloroform layer discarded. The aqueous layer was filtered and then made basic by the addition of solid sodium bicarbonate in which the ergoline bases were insoluble. The aqueous layer was extracted with chloroform and the chloroform layer separated and dried, and the chloroform removed by evaporation in vacuo. Chromatography of the resulting residue over florisil using chloroform as the eluant yielded fractions containing, as a predominant spot on thin-layer chromatography, a material other than starting material. These fractions were combined, the solvent removed by evaporation in vacuo, and the resulting residue recrystallized from ether to yield D-2-bromo-6-methyl-8-bromomethylergoline produced in the above reaction. The compound melted at about 215° C. with decomposition.

Analysis: Calc: C, 48.27; H, 4.56; N, 7.04; Br, 40.14. Found: C, 48.01; H, 4.66; N, 7.16; Br, 40.38.

90 mg. of D-2-bromo-6-methyl-8-bromomethylergoline prepared as above were dissolved in 10 ml. of dimethylsulfoxide (DMSO). 100 mg. of sodium cyanide were added and the resulting mixture heated at 105° C. under a nitrogen atmosphere for about 45 minutes. The reaction mixture was cooled, diluted with water and filtered. The filter cake was dissolved in an ethanol-chloroform solvent mixture, and the solvents removed by evaporation in vacuo. Recrystallization of the residue from ether yielded D-2-bromo-6-methyl-8-cyanomethylergoline prepared in the above reaction. The compound melted at about 240–3° C. with decomposition.

Following the above procedure, D-6-methyl-8-mesyloxymethylergoline (from Example 4) can be halogenated in the 2-position by the procedure of Example 1 to yield D-2-chloro-6-methyl-8-mesyloxymethylergoline, D-2-bromo-6-methyl-8-mesyloxymethylergoline or D-2-iodo-6-methyl-8-mesyloxymethylergoline, each of which can in turn be converted to the 8-cyanomethyl derivative by reaction with sodium cyanide as above.

The 8-tosyloxymethyl derivatives, prepared by substituting p-toluenesulfonyl chloride for methanesulfonyl chloride in the procedure of Example 4, can be halogenated in the 2-position and the 2-halo derivative reacted with sodium cyanide to yield the same compounds.

EXAMPLE 6

Preparation of D-2-chloro-6-ethyl-8-cyanomethylergoline

A solution was prepared containing 6.11 g. of D-2-chloro-6-methyl-8-cyanomethylergoline (as furnished by the procedure of Example 1) in 1000 ml. of methylenedichloride. 13.5 g. of cyanogen bromide were added, and the reaction mixture stirred at room temperature under anhydrous conditions for 69 hours. The reaction mixture was poured into aqueous tartaric acid and the acidic solution extracted with chloroform. The chloroform layer was separated, washed with water and dried. Evaporation of the chloroform yielded a residue comprising D-2-chloro-6-cyano-8-cyanomethylergoline formed in the above reaction. Recrystallization of the residue from ethanol yielded purified D-2-chloro-6-cyano-8-cyanomethylergoline melting at about 231-2° C.

Analysis: Calc: C, 65.70; H, 4.87; N, 18.03; Cl, 11.41. Found: C, 65.46; H, 4.61; N, 18.01; Cl, 11.49.

A mixture of 5.4 g. of D-2-chloro-6-cyano-8-cyanomethylergoline, 30 g. of zinc dust, 2210 ml. of glacial acetic acid and 45 ml. of water was refluxed under a nitrogen atmosphere for 8 hours. The reaction mixture was filtered, and the filtrate dilute with water and then made basic by the addition of 14N aqueous ammonium hydroxide. The alkaline solution was extracted with chloroform, the chloroform layer separated, washed with water and dried, and the chloroform evaporated therefrom by evaporation in vacuo. The resulting residue, comprising D-2-chloro-8-cyanomethylergoline formed in the above reaction, was recrystallized from ethanol to yield crystals melting at 228-9° C. with decomposition.

Analysis: Calc., C, 67.24; H, 5.64; N, 14.70; Cl, 12.41. Found: C, 66.99; H, 5.40; N, 14.87; Cl, 12.42.

About 300 mg. of D-2-chloro-8-cyanomethylergoline were dissolved in 10 ml. of DMF (dimethylformamide). 220 mg. of potassium carbonate were added to the reaction mixture, followed by 0.12 ml. of ethyl iodide. The reaction mixture was stirred at room temperature under a nitrogen atmosphere for 5.5 hours. The reaction mixture was then diluted with water, and the aqueous layer extracted with ethyl acetate. The ethyl acetate layer was separated, washed with water, followed by a wash with saturated aqueous sodium chloride and was then dried. Evaporation of the ethyl acetate in vacuo yielded D-2-chloro-6-ethyl-8-cyanomethylergoline melting at 225-7° C. with decomposition after chromatography over florisil using chloroform containing 2 percent ethanol as the eluting solvent.

Analysis: Calc: C, 68.89; H, 6.42; N, 13.39; Cl, 11.30. Found: C, 68.64; H, 6.15; N, 13.45; Cl, 11.37.

Following the above procedure but substituting the appropriate alkyl halide for ethyl iodide, the following compound was prepared: D-2-chloro-6-n-propyl-8-cyanomethylergoline melting at 185-7° C.

Analysis: Calc: C, 69.61; H, 6.76; N, 12.82; Cl, 10.81. Found: C, 69.57; H, 6.98; N, 12.59; Cl, 10.64.

Alkylation of D-2-chloro-8-cyanomethylergoline with methyl iodide in the presence of potassium carbonate in DMF solution yields D-2-chloro-6-methyl-8-cyanomethylergoline. The compound has identical properties to the starting material provided for this series of reactions in Example 1.

Following the above procedure, D-2-chloro-6-methyl-8-carboxyamidomethylergoline has been demethylated, and the resulting secondary amine alkylated to yield higher alkyl analogs as, for example, D-2-chloro-6-ethyl-8-carboxyamidomethylergoline and D-2-chloro-6-n-propyl-8-carboxyamidomethylergoline. Similarly 8-cyanomethyl or 8-carboxamidomethylergolines having groups in the 2 position of the ergoline ring other than chloro as, for example, the 2-bromo, 2-iodo, 2-methyl or 2-cyano derivatives, can also be demethylated to yield the corresponding secondary amine which compound can in turn be realkylated to yield higher homologs as in the D-2-chloro-8-cyanomethyl reaction series outlined above in Example 6.

Salts of the compounds of this invention (Formula II above) with pharmaceutically-acceptable acids can be prepared by dissolving a quantity of the particular ergoline base in ether and adding the pharmaceutically-acceptable acid in an equivalent amount also in ethanol solution. In this instance, the salts are generally soluble and are recovered by removal of the solvent by evaporation in vacuo. The resulting residue, if not crystalline, can be readily crystallized from ethanol or other suitable solvent.

PREPARATION OF SALTS

A solution containing 560 mg. of D-2-bromo-6-methyl-8-cyanomethylergoline in about 40 ml. of tetrahydrofuran (THF) was prepared. About 10 ml. of a solution prepared by dissolving 1 g. of maleic acid in 50 ml. of THF was added with stirring to the solution of the ergoline base. About 200 ml. of ether were added, and the resulting precipitate separated by filtration. D-2-bromo-6-methyl-8-cyanomethylergoline acid maleate thus prepared melted at about 207°-209° C. with decomposition.

Following the above procedure, D-2-chloro-6-methyl-8-cyanomethylergoline acid maleate was prepared melting at about 204°-206° C. with decomposition.

Following the above procedure, 320 mg. of D-2-chloro-6-methyl-8-cyanomethylergoline were dissolved in 15 ml. of THF. To this solution was added a solution of methanesulfonic acid in THF, 1 drop at a time, until the addition of a drop gave no further precipitate. The THF solution was diluted with ether, and the resulting mixture filtered to yield the methanesulfonic acid salt of D-2-chloro-6-methyl-8-cyanomethylergoline melting at about 295° C. with decomposition after recrystallization from an ethanol-ether solvent mixture.

Analysis: Calc: C, 54.61; H, 5.60; N, 10.61; Cl, 8.95; S, 8.10. Found: C, 54.43; H, 5.79; N, 10.86; Cl, 9.22; S, 8.18.

Following the above procedure, 220 mg. of D-2-chloro-6-methyl-8-cyanomethylergoline were dissolved in 15 ml. of THF. An excess of a saturated solution of d-tartaric acid in THF was added. A gelatinous precipitate resulted which slowly crystallized. The mixture was diluted with ether and filtered to yield the tartrate salt of D-2-chloro-6-methyl-8-cyanomethylergoline melting at about 247-9° C. after recrystallization from an ethanol-ether solvent mixture.

Analysis: Calc: C, 60.88; H, 5.65; N, 11.21; Cl, 9.46. Found: C, 60.66; H, 5.41; N, 11.41; Cl, 9.49.

The compounds of Formula II above are useful as prolactin inhibitors. The compounds are thus useful in the treatment of inappropriate lactation such as postpartum lactation and galactorrhea. In addition, the compounds can be used to treat prolactin-dependent adenocarcinomas and prolactin-secreting pituitary tumors.

In carrying out my novel control method, using the compounds of this invention to inhibit prolactin secretion, a 2,8-disubstituted-6-alkylergoline according to Formula II above or a salt thereof with a pharmaceutically-acceptable acid is suspended in corn oil and the suspension injected parenterally or fed to a female mammal in amounts varying from 0.01 to 10 mg/kg/day of mammalian weight. Oral administration is preferred. If parenteral administration is used, the injection is preferably by the subcutaneous route using an appropriate pharmaceutical formulation although other modes of parenteral administration such as intraperitoneal, intramuscular, or intravenous routes are equally effective. In particular, with intravenous or intramuscular administration, a soluble pharmaceutically-acceptable salt of a 2-substituted-6-alkyl-8-cyanomethyl-ergoline, preferably the methanesulfonate salt, is customarily employed. For oral administration, a compound according to Formula II either as the free base or in the form of a salt thereof can also be mixed with standard pharmaceutical excipients and loaded into empty telescoping gelatin capsules or pressed into tablets. The inhibition of prolactin secretion by the compounds of Formula II is evidenced by the following experiment: Groups of lactating postpartum female rats were administered the drug at 4 to 8 days potapartum (delivery equals day 0). A control group received only 0.2 ml. of corn oil daily, and the other groups received D-2-bromo-6-methyl-8-cyanomethylergoline or the corresponding chloro compound at different dose levels. At the beginning of treatment, the rat litters were reduced to six pups each and the total weight of each litter recorded. Both litters and lactating females were weighed on days 4, 6, and 8. On day 8 the lactating females were taken from their suckling litters and immediately decapitated. The blood was collected and the resulting serum assayed by a radioimmunoassay for prolactin content. The table which follows records results of this experiment. In the Table, column 1 gives the treatment administered, column 2 the number of rats in the treated group, column 3 the average weight changes of the reduced litter, column 4 the average body weight change of the lactating female, and column 5 the average serum prolactin levels on day 8.

tors, showing an inhibition of prolactin comparable to that given in Table 1 for D-2-bromo-6-methyl-8-cyanomethylergoline and D-2-chloro-6-methyl-8-cyanomethylergoline. In particular, the 6-ethyl and 6-n-propyl analogs showed a comparable prolactin inhibition activity to that of the 6-methyl compound.

A further test to measure the ability of the ergolines of Formula II to inhibit prolactin secretion was carried out by the following procedure:

Adult male rats of the Spraque-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the ergoline derivative. The purpose of the reserpine was to keep prolactin levels uniformly elevated. The compounds under test were dissolved in 10 percent ethanol at a concentration of 10 mcg/ml. and were injected intraperitoneally at a standard dose of 50 mcg/kg. Each compound was administered to a group of 10 rats, and a control group of 10 intact males received an equivalent amount of 10 percent ethanol. One hour after treatment all rats were killed by decapitation, and 150 ul aliquots of serum were assayed for prolactin. The results were evaluated statistically using Student's "t" test to calculate the level of significance, "p".

The difference between the prolactin level of the treated rats and prolactin level of the control rats, divided by the prolactin level of the control rats gives the percent inhibition of prolactin secretion attributable to the compounds of this invention. These inhibition percentages are given in Table 2 below. In the table, column 1 gives the name of the compound; column 2, the Table 1

| Treatment (Day 4 - Day post partum) | No. of Rats | Avg. Weight Change of Reduced Litter (Day 4 - Day 8) | Avg. Body Weight Change of Lactating Female | Avg. Serum Prolactin Levels of Lactating Females - (Day 8) |
|---|---|---|---|---|
| Control Corn Oil (0.2 ml/da) | 30 | +43.8 ± 1.9 gm | +11.3 ± 3.2 gm | 60.6 ± 4.8 ng/ml |
| D-2-Bromo-6-methyl-8B-cyanomethyl-ergoline- (0.6 mg/da) | 11 | +24.9 ± 4.2*gm | +18.5 ± 5.1 gm$^{NS}$ | 11.9 ± 1.9 ng/ml* |
| D-2-bromo-6-methyl-8B-cyanomethyl-ergoline (1.0 mg/da) | 10 | +14.8 ± 2.0*gm | + 3.9 ± 4.0 gm$^{NS}$ | 12.4 ± 1.3 ng/ml*a |
| D-2-Chloro-6-methyl-8B-cyanomethyl-ergoline (0.6 mg/da) | 11 | + 5.5 ± 2.6*gm | + 0.9 ± 4.7 gm$^{NS}$ | 11.8 ± 1.0 ng/ml* |

*Significantly different from controls P<.001
$^{NS}$Not significantly different
a This value based on 5 animals As can be seen from the above table, the two compounds coming within the scope of Formula II above greatly decreased the prolactin levels and thus the prolactin secretion in the lactating female rats.

Other compounds coming within the scope of formula II above are extremely effective prolactin inhibitors, showing dose level of the compound in the prolactin inhibition test; column 3, the prolactin levels for the group of rats given a saline control injection; column 4, the prolactin level for the group after injection with the trial compound; column 5, the percent prolactin inhibition; and column 6, the level of significance.

Table 2

| EFFECT OF ERGOLINES ON PROLACTIN LEVELS IN RESERPINIZED MALE RATS | | | | | |
|---|---|---|---|---|---|
| | | Serum Prolactin Levels ng/nl. | | | Statistics |
| Compound Name | Dose | Saline Control | Compound Treated | % Change (Control-Treated) | Significance of Difference Control vs. Treated* |
| D-2-Cl-6-methylergoline 8β-acetonitrile | 10μg | 30.8 ± 3.5 | 14.2 ± 1.6 | −54% | t = 4.3  P<0.001 |
| D-2-Cl-6-methylergoline-8β-acetonitrile methane sulfonic acid salt | 10μg | 32.4 ± 2.7 | 10.9 ± 0.4 | −66% | t = 7.9  P<0.001 |
| D-2-bromo-6-methylergoline- | 10μg | 24.5 ± 3.1 | 11.4 ± 1.1 | −53% | t = 4.1  P<0.001 |

Table 2-continued
EFFECT OF ERGOLINES ON PROLACTIN LEVELS IN RESERPINIZED MALE RATS

| Compound Name | Dose | Serum Prolactin Levels ng/nl. Saline Control | Serum Prolactin Levels ng/nl. Compound Treated | % Change (Control-Treated) | Statistics Significance of Difference Control vs. Treated* | |
|---|---|---|---|---|---|---|
| 8β-acetonitrile D-2-iodo-6-methylergoline-8β-acetonitrile | 10μg | 30.8 ± 3.5 | 17.1 ± 0.6 | −44% | t = 3.8 | P<0.01 |
| D-2-Cl-6-ethylergoline-8β-acetonitrile | 10μg | 50.6 ± 5.3 | 12.0 ± 1.3 | −76% | t = 7.0 | P<0.001 |
| D-2-Cl-6-n-propylergoline-8β-acetonitrile | 10μg | 32.7 ± 2.3 | 8.6 ± 0.6 | −74% | t = 10 | P<0.001 |

*Students t test P<0.05 is considered representative of a significant difference.

The compounds of this invention according to Formula II wherein R' is $C_1$-$C_3$ primary alkyl have a greatly decreased toxicity as compared with those compounds of the prior art in which the 2-position in unsubstituted. For example, acute toxicity studies in mice indicate that the D-2-halo-6-methyl-8-cyanomethyl (or 8-carboxamidomethyl)ergolines have an $LD_{50}$ in the neighborhood of 1,000 mg/kg in mice. On the other hand, D-6-methyl-8-cyanomethylergoline has an $LD_{50}$ of about 100 mg/kg in mice. Acid addition salts of D-2-halo-6-alkyl-8cyanomethyl (or 8-carboxamidomethyl)ergolines are somewhat more toxic then the free bases since they are more readily absorbed. For example, D-2-chloro-6-methyl-8-cyanomethylergoline methane sulfonate had an acute oral toxicity as follows: $LD_{50}$=250–300 mg./kg. Furthermore, daily subcutaneous doses to rats as high as 7 mg./kg. showed little or no toxicity as shown by loss of weight. As prolactin inhibitors, however, the 2-halo substituted compounds of this invention were at least equally potent to the unsubstituted D-6-methyl-8-cyanomethyl(or 8-carboxamidomethyl)ergolines of the prior art.

We claim:

1. A process for inhibiting the secretion of prolactin in mammals which comprises administering from 0.01 to 10 mg/kg/day of mammalian weight of a compound of Formula II or a salt thereof formed with a pharmaceutically-acceptable acid, to a mammal having a condition in which there is an excess of prolactin being secreted:

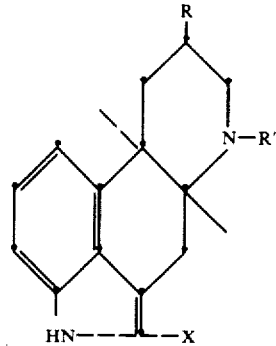

II wherein X is Cl, Br or I, R is $CH_2$—CN or

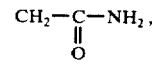

and R' is $C_1$-$C_3$ primary alkyl.

2. A process according to claim 1 in which D-2-chloro-6-methyl-8-cyanomethylergoline methanesulfonate is administered.

* * * * *